Figure 1:
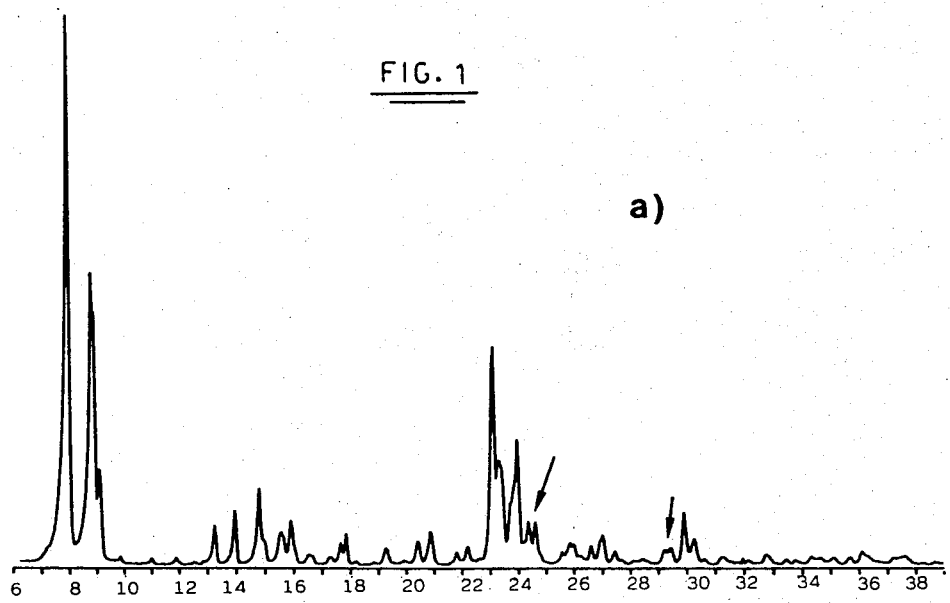
Figure 1:
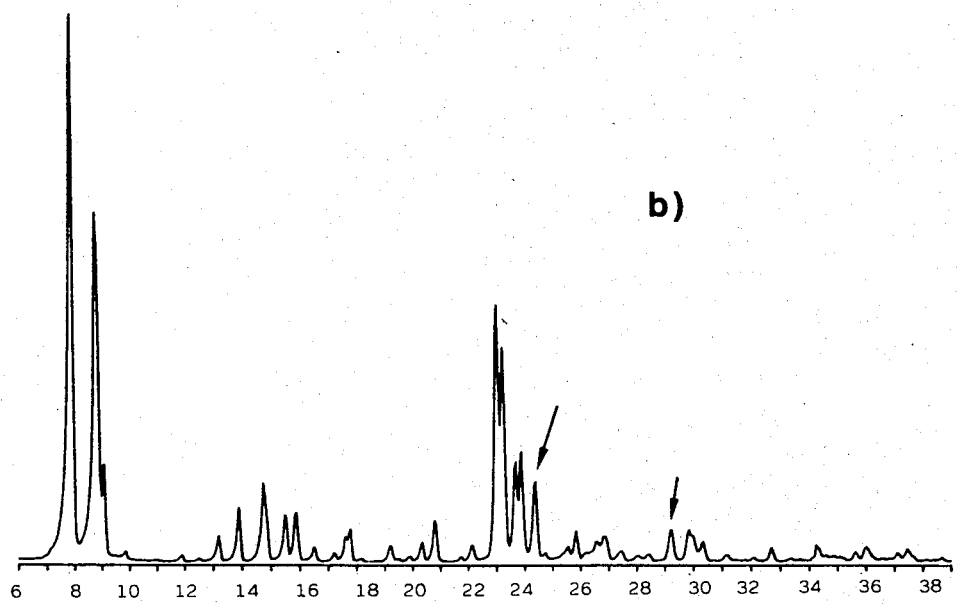

United States Patent [19]

Neri et al.

[11] Patent Number: 4,495,371

[45] Date of Patent: Jan. 22, 1985

[54] PROCESS FOR ISOMERIZING STYRENE OXIDE OR HOMOLOGUES TO β-PHENYLALDEHYDES

[75] Inventors: Carlo Neri; Franco Buonomo, both of S. Donato Milanese, Italy

[73] Assignee: ANIC S.p.A., Palermo, Italy

[21] Appl. No.: 513,800

[22] Filed: Jul. 14, 1983

[30] Foreign Application Priority Data

Jul. 28, 1982 [IT] Italy ............................... 22606 A/82

[51] Int. Cl.³ .............................................. C07C 45/58
[52] U.S. Cl. .................................................... 568/427
[58] Field of Search ........................ 568/427, 450, 483

[56] References Cited

U.S. PATENT DOCUMENTS

| | | | |
|---|---|---|---|
| 2,628,255 | 2/1953 | Sexton et al. | 568/427 |
| 2,694,090 | 11/1954 | Wild et al. | 568/450 |
| 3,067,256 | 12/1962 | Fischer et al. | 568/427 X |
| 3,855,303 | 12/1974 | Bishop | 568/450 X |
| 3,927,110 | 12/1975 | Watson | 568/427 |

*Primary Examiner*—Bernard Helfin
*Attorney, Agent, or Firm*—Hedman, Gibson, Costigan & Hoare

[57] ABSTRACT

A process for isomerizing styrene or homologues to β-phenylaldehydes, consisting of conducting the isomerization reaction in the presence of a catalyst constituted by synthetic zeolites containing titanium, of formula $$xTiO_2 \cdot (1-x)SiO_2$$

where x lies between 0.0001 and 0.04, and optionally in the presence of one or more solvents, operating at a temperature of between 30° and 100° C.

7 Claims, 2 Drawing Figures a)

b)

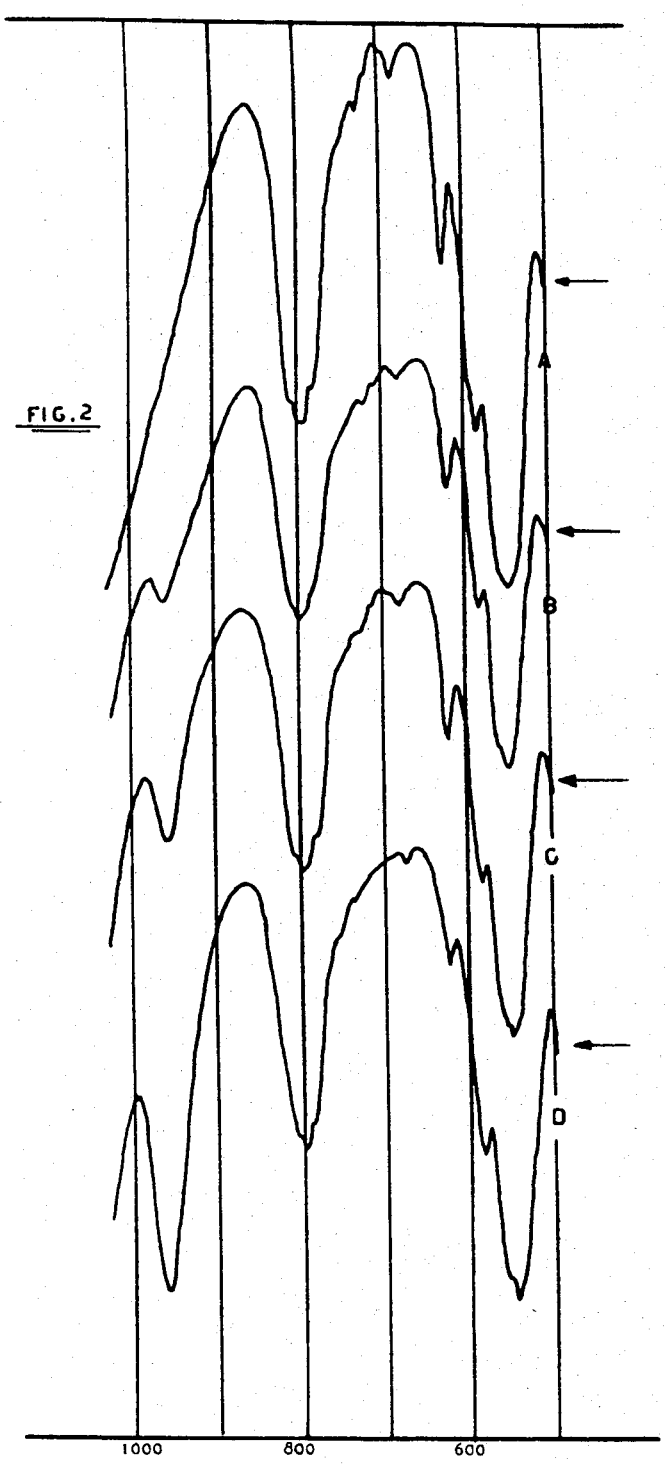

PROCESS FOR ISOMERIZING STYRENE OXIDE OR HOMOLOGUES TO β-PHENYLALDEHYDES

This invention relates to a process for isomerising styrene oxide or homologues to β-phenylaldehydes, using a synthetic zeolite as catalyst.

Various processes are known for obtaining β-phenylaldehydes from styrene oxide. In U.S. Pat. No. 3,927,110, the styrene oxide is reacted in the presence of an aryl or alkylaryl sulphate of an alkaline-earth metal at a temperature of between 125° and 450° C., to give β-phenylaldehydes. In Japanese patent application No. 49/051233, a suspension of clay in an organic solvent is added to the styrene oxide in order to effect the isomerisation. In Japanese patent application No. 74/025932, the styrene oxide is isomerised using kaolin as catalyst, and operating at a temperature of 180° C. These processes have the drawback of poor yields.

We have surprisingly found that a synthetic zeolite containing titanium atoms is able to selectively isomerise styrene oxide or homologues, with high yields of β-phenylaldehydes. The subject matter of the present invention is a process for isomerising styrene oxide or homologues to β-phenylaldehydes, consisting of conducting the isomerisation reaction in the presence of a catalyst constituted by synthetic zeolites containing titanium atoms (titanium silicalites), of the following general formula:

$$xTiO_2.(1-x)SiO_2,$$

where x lies between 0.0001 and 0.04, and possibly in the presence of one or more solvents. Titanium silicalite is indicated hereinafter as TS-1.

The synthetic zeolites used for the epoxidation reaction are described in Belgian Pat. No. 886,812, of which we repeat some points illustrating the material and relative method of preparation. The composition range of the titanium silicalite expressed in terms of molar ratios of the reagents is as follows:

| Molar ratio of reagents | | preferably |
|---|---|---|
| SiO$_2$/TiO$_2$ | 5–200 | 35–65 |
| OH$^-$/ SiO$_2$ | 0.1–1.0 | 0.3–0.6 |
| H$_2$O/SiO$_2$ | 20–200 | 60–100 |
| Me/SiO$_2$ | 0.0–0.5 | 0 |
| RN$^+$/SiO$_2$ | 0.1–2.0 | 0.4–1.0 |

RN$^+$ indicates the nitrogenated organic cation deriving from the organic base used for the preparation of the titanium silicalite (TS-1). Me is an alkaline ion, preferably Na or K.

The final TS-1 has a composition satisfying the formula $xTiO_2.(1-x)SiO_2$, where x lies between 0.0001 and 0.04, and preferably between 0.01 and 0.025. The TS-1 is of the silicalite type, and all the titanium substitutes the silicon.

The synthetic material has characteristics which are shown up by X-ray and infrared examination. The X-ray examination is carried out by means of a powder diffractometer provided with an electronic pulse counting system, using the radiation CuK$\alpha$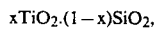. The titanium silicalites (TS-1) are characterised by a X-ray diffraction spectrum as shown in FIG. 1b. This spectrum is similar overall to the typical spectrum of silicalite (FIG. 1a), however it has certain clearly "single" reflections where double reflections are evident in the pure silicalite spectrum.

Because the spectral differences between TS-1 and silicalite are relatively small, special accuracy is required in the spectral determination. For this reason TS-1 and silicalite were examined by the same apparatus, using Al$_2$O$_3$ as the internal standard. Table 1 shows the most significant spectral data of a TS-1 where x=0.017, and of a pure silicalite. The constants of the elementary crystalline cell were determined by the minimum square method, on the basis of the interplanar distances of 7–8 single reflections lying within the range of 10°–40° 2θ.

A large proportion of the interplanar distances of TS-1 are tendentially greater than the corresponding distances of pure silicalite, although only slightly, which is in accordance with the larger predictable value of the Ti—O bond distance relative to that of the Si—O bond distance. Passage from a double reflection to a single reflection is interpreted as a change from a monoclinic symmetry (pseudo orthorhombic) (silicalite) to an effective orthorhombic symmetry, "titanium silicalite" (TS-1). In FIG. 1, the most apparent aforesaid spectral differences are indicated by arrows.

INFRARED EXAMINATION

TS-1 shows a characteristic absorption band at about 950 cm$^{-1}$ (see FIG. 2, spectra B, C and D) which is not present in the pure silicalite spectrum (FIG. 2, spectrum A), and is also absent in titanium oxides (rutile, anastase) and in alkaline titanates. Spectrum B is that of TS-1 with 5 mol% of TiO$_2$, spectrum C is that of TS-1 with 8 mol% of TiO$_2$, and spectrum D is that of TS-1 with 2.3 mol% of TiO$_2$.

As can be seen from FIG. 2, the band intensity at approximately 950 cm$^{-1}$ increases with the quantity of titanium which substitutes the silicon in the silicalite structure.

MORPHOLOGY

From a morphological aspect, TS-1 is in the form of parallelepipeds with chamfered edges. A X-ray microprobe examination has shown that the titanium distribution within the crystal is perfectly uniform, thus confirming that the titanium substitutes the silicon in the silicalite structure, and is not present in other forms.

The process for preparing titanium silicalite comprises the preparation of a reaction mixture consisting of sources of silicon oxide, titanium oxide and possibly an alkaline oxide, a nitrogenated organic base and water, the composition in terms of the molar reagent ratios being as heretofore defined.

The silicon oxide source can be a tetraalkylorthosilicate, preferably tetraethylorthosilicate, or simply a silicate in colloidal form, or again a silicate of an alkaline metal, preferably Na or K. The titanium oxide source is a hydrolysable titanium compound preferably chosen from TiCl$_4$, TiOCl$_2$ and Ti(alkoxy)$_4$, preferably Ti(OC$_2$H$_5$)$_4$.

The organic base is tetraalkylammonium hydroxide, and in particular tetrapropylammonium hydroxide.

The reagent mixture is subjected to hydrothermal treatment in an autoclave at a temperature of between 130° and 200° C. under its own developed pressure, for a time of 6–30 days until the crystals of the TS-1 precursor are formed. These are separated from the mother solution, carefully washed with water and dried. When in the anhydrous state they have the following composition:

$$xTiO_2 \cdot (1-x)SiO_2 \cdot 0.04(RN^+)_2O.$$

The precursor crystals are heated for between 1 and 72 hours in air at 550° C. to completely eliminate the nitrogenated organic base. The final TS-1 has the following composition: $xTiO_2 \cdot (1-x)SiO_2$, where x is as heretofore defined. Chemical and physical examinations are carried out on the products thus obtained.

The isomerisation reaction is carried out at a temperature of between 30° and 100° C., and preferably between 60° and 80° C. Styrene oxide homologues are all those which satisfy the general formula:

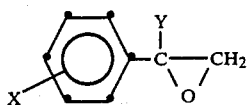

where X can be H, an alkyl radical or oxygen bonded to an alkyl radical, the alkyl radical having between 1 and 20 carbon atoms, and Y can be H or CH$_3$. On isomerisation of these compounds, β-phenylaldehydes are obtained of formula:

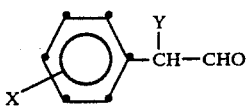

where X and Y are as heretofore specified. The reaction can be carried out in mass or in the presence of a suitable solvent.

The solvent used can be any polar compound such as alcohols, ketones, esters, glycols or acids, with a number of carbon atoms which is not too high, and preferably less than or equal to 6.

Methanol is the most preferred of the alcohols, and acetone the most preferred of the ketones. Some examples are described hereinafter illustrating the manner of operating the process according to the present invention, which however must not be considered limited to them or by them.

EXAMPLES 1-12

100 cc of solvent, 50 g of epoxide and 3 g of catalyst are fed into a 250 cc glass flask fitted with a reflux condenser and magnetic stirrer. The flask is immersed in a bath temperature-controlled at 70° C. under stirring, and the disappearance of the epoxide and the formation of the aldehyde are followed by withdrawing samples with time and analysing them by gas chromatography. On completion of the reaction, the mixture is cooled and qualitative and quantitative GLC and gas mass analyses are carried out. The results are indicated in Table 2.

TABLE I

| | TS - 1 | | | Silicate[a] | | |
|---|---|---|---|---|---|---|
| 2θ (Cukα) | Interplanar distance d(Å) | Rel. Int.[b] | | 2θ (Cukα) | Interplanar distance d(Å) | Rel. Int.[b] |
| 7.94 | 11.14 | vs | | 7.94 | 11.14 | vs |
| 8.85 | 9.99 | s | | 8.85 | 9.99 | s |
| 9.08 | 9.74 | m | | 9.08 | 9.74 | m |
| 13.21 | 6.702 | w | | 13.24 | 6.687 | w |
| 13.92 | 6.362 | mw | | 13.95 | 6.348 | mw |
| 14.78 | 5.993 | mw | | 14.78 | 5.993 | mw |
| 15.55 | 5.698 | w | | 15.55 | 5.698 | w* |
| 15.90 | 5.574 | w | | 15.90 | 5.574 | w |
| 17.65 | 5.025 | w | | 17.65 | 5.025 | w |
| 17.81 | 4.980 | w | | 17.83 | 4.975 | w |
| 20.37 | 4.360 | w | | 20.39 | 4.355 | w |
| 20.85 | 4.260 | mw | | 20.87 | 4.256 | mw |
| 23.07 | 3.855 | s | | 23.08 | 3.853 | s |
| | | | | 23.28 | 3.821 | ms |
| 23.29 | 3.819 | s | | | | |
| | | | | 23.37 | 3.806 | ms |
| | | | | 23.71 | 3.753 | ms |
| 23.72 | 3.751 | s | | | | |
| | | | | 23.80 | 3.739 | ms |
| 23.92 | 3.720 | s | | 23.94 | 3.717 | s |
| | | | | 24.35 | 3.655 | mw |
| 24.41 | 3.646 | m | | | | |
| | | | | 24.60 | 3.619 | mw |
| | | | | 25.84 | 3.448 | w |
| 25.87 | 3.444 | w | | | | |
| | | | | 25.97 | 3.431 | w |
| 26.87 | 3.318 | w* | | 26.95 | 3.308 | w* |
| | | | | 29.23 | 3.055 | w |
| 29.27 | 3.051 | mw | | | | |
| | | | | 29.45 | 3.033 | w |
| 29.90 | 2.988 | mw | | 29.90 | 2.988 | mw |
| 30.34 | 2.946 | w | | 30.25 | 2.954 | w |
| 45.00 | 2.014 | mw* | | 45.05 | 2.012 | mw* |
| 45.49 | 1.994 | mw* | | 45.60 | 1.989 | mw* |

[a] Prepared by the method of U.S. Pat. No. 4,061,724; product calcined at 550° C.
[b] vs: very strong; s: strong; ms: medium strong; m: medium; mw: medium weak; w: weak; *: multiplet.

TABLE 2

| Ex. No. | EPOXIDE | TIME (hours) | SOLVENT | EPOXIDE CONVERSION % | ALDEHYDE SELECTIVITY % |
|---|---|---|---|---|---|
| 1 | STYRENE | 1 | METHANOL | 100 | 95 |
| 2 | STYRENE | 1 | ACETONE | 100 | 98.2 |
| 3 | STYRENE | 1 | — | 70 | 99 |
| 4 | α-METHYLSTYRENE | 1.5 | METHANOL | 93 | 90 |
| 5 | α-METHYLSTYRENE | 1.5 | ACETONE | 97 | 95.5 |
| 6 | α-METHYLSTYRENE | 1.5 | — | 50 | 98 |
| 7 | 4-METHYLSTYRENE | 1.2 | METHANOL | 100 | 94 |
| 8 | 4-METHYLSTRYENE | 1.2 | ACETONE | 98 | 96.2 |
| 9 | 4-METHYLSTYRENE | 1.5 | — | 60 | 98.3 |
| 10 | 4-METHOXYSTYRENE | 1.3 | METHANOL | 100 | 93 |
| 11 | 4-METHOXYSTYRENE | 1.5 | ACETONE | 100 | 96 |
| 12 | 4-METHOXYSTYRENE | 1.6 | — | 50 | 98.5 |

Aldehyde selectivity is given by: $\frac{\text{moles of aldehyde formed}}{\text{moles of epoxide transformed}} \times 100$ Epoxide conversion is given by: $\frac{\text{moles of epoxide transformed}}{\text{moles of epoxide fed}} \times 100$

We claim:
1. A process for the isomerisation of styrene oxide or homologs thereof to the corresponding β-phenylaldehydes comprising conducting the isomerisation reaction in the presence of a catalyst composed of synthetic zeolites containing titanium, said zeolites being of the general formula:

$$xTiO_2 \cdot (1-x)SiO_2$$

where x is between 0.0001 and 0.04, and optionally in the presence of one or more solvents.

2. A process as claimed in claim 1, characterised in that the isomerisation is conducted at a temperature of between 30° and 100° C.

3. A process as claimed in claim 2, wherein the temperature lies between 60° and 80° C.

4. A process as claimed in claim 1, wherein the solvent is polar.

5. A process as claimed in claim 4, wherein the polar solvent is chosen from alcohols, glycols, ketones, esters and acids, which have a number of carbon atoms less than or equal to 6.

6. A process as claimed in claim 5, wherein the alcohol is methanol.

7. A process as claimed in claim 5, wherein the ketone is acetone.

* * * * *